United States Patent [19]

Beilfuss et al.

[11] Patent Number: 4,917,815

[45] Date of Patent: Apr. 17, 1990

[54] STABLE AQUEOUS AROMATIC PERCARBOXYLIC ACID SOLUTION

[75] Inventors: Wolfgang Beilfuss, Hamburg; Karl-Heinz Diehl, Norderstedt, both of Fed. Rep. of Germany

[73] Assignee: Sterling Drug Inc., New York, N.Y.

[21] Appl. No.: 205,133

[22] Filed: Jun. 10, 1988

[51] Int. Cl.$^4$ .................. C07C 179/133; D06L 3/02; A01N 37/10; A01N 43/40

[52] U.S. Cl. .................. 252/186.23; 252/186.26; 252/186.28; 252/186.29; 424/616; 514/461; 514/568; 514/714

[58] Field of Search ............. 252/186.22, 186.23, 252/186.26, 186.27, 186.28, 186.29, 186.42

[56] References Cited

U.S. PATENT DOCUMENTS

| | | | |
|---|---|---|---|
| 3,248,336 | 4/1966 | Blumbergs | 252/186.26 |
| 3,756,775 | 9/1973 | Nordfalt | 252/186.23 X |
| 3,864,271 | 2/1975 | Stalter | 252/186.29 X |
| 4,129,517 | 12/1978 | Eggensperger et al. | 252/186.23 |
| 4,221,660 | 9/1980 | Eggensperger et al. | 210/764 |
| 4,259,383 | 3/1981 | Eggensperger et al. | 428/72 |
| 4,287,135 | 9/1981 | Stober et al. | 252/186.26 X |

FOREIGN PATENT DOCUMENTS

| | | |
|---|---|---|
| P3543500 | 6/1987 | Fed. Rep. of Germany . |
| 1566671 | 5/1980 | United Kingdom . |

OTHER PUBLICATIONS

Ullmans Enzyklopadie der Technischen, Chemie, 4th Edition, Verlag Chemie, pp. 669-670.

Primary Examiner—Brooks H. Hunt
Assistant Examiner—Virginia B. Caress
Attorney, Agent, or Firm—Frederik W. Stonner; Paul E. Dupont

[57] ABSTRACT

Aqueous solutions of aromatic percarboxylic acids, such as perbenzoic acids, stabilized with at least an equal amount in parts by weight as the amount of aromatic percarboxylic acid of the corresponding aromatic carboxylic acid and an aqueous solution of perglutaric acid stabilized with hydrogen peroxide and/or a 10% to 60% aqueous solution of hydrogen peroxide.

7 Claims, No Drawings

STABLE AQUEOUS AROMATIC PERCARBOXYLIC ACID SOLUTION

BACKGROUND OF THE INVENTION

1. Field of the Invention

The invention relates to an aqueous solution of an aromatic percarboxylic acid which has been stabilized with at least an equal amount of the aromatic carboxylic acid corresponding to the aromatic percarboxylic acid and with an aqueous solution of perglutaric acid stabilized by means of excess $H_2O_2$ and/or with a 10% to 60% strength solution of $H_2O_2$, and also to the use thereof as a disinfectant or bleaching agent.

2. Information Disclosure Statement

Aromatic percarboxylic acids are known to be highly effective biocides having a broad spectrum of activity as well as bleaching and oxidizing agents (see U.S. Pat. Nos. 3,248,336 and 4,221,660). Aromatic percarboxylic acids can be prepared by reaction of the corresponding aromatic carboxylic acid or a corresponding activated carboxylic acid derivative such as, for example, an aromatic carboxylic anhydride, with hydrogen peroxide in aqueous solution (see Ullman's Enzyklopadie der Technischen Chemie, Vierte Ansgabe, Verlag Chemie, Band 17, Seiten 669–670).

As a practical matter, however, aromatic percarboxylic acids are seldom employed, because their solubility in water-based formulations is too low and their stability in aqueous solutions is not satisfactory. Although, with the exception of perbenzoic acid, aromatic percarboxylic acids are adequately stable in solid form, they can seldom be employed in practice due to their low solubility and speed of solution in liquid use formulations. Admittedly attempts have been made, as described in U.S. Pat. No. 3,248,336, to employ aromatic percarboxylic acids in aqueous solutions of bleaching agents containing tert-butyl alcohol and water in a 1:1 ratio. Such solutions are, however, unsuitable because of their odor, the volatility of the tert-butyl alcohol present in a relatively high concentration and their low flash point. Attempts also have been made to employ as disinfectants saturated aqueous solutions of substituted aromatic percarboxylic acids containing an undissolved excess of the percarboxylic acids (see U.S. Pat. No. 4,221,660). Such solutions have not met with success in practice, since the percarboxylic acids themselves are not adequately stable under these conditions.

Finally, from British Pat. No 1,566,671 it is known to employ solid mixtures of an activated aromatic carboxylic acid derivative, such as, for example, a carboxylic acid ester, and a source of $H_2O_2$, such as, for example, sodium percarbonate, together with further additives necessary for storage stability, to produce disinfectant solutions of aromatic percarboxylic acids when dissolved in water. The disadvantages of such mixtures are the handling of dust-forming powders, the slow rate of solution and the limited stability of the use solutions derived therefrom, which must have a relatively high pH because of the reaction of the carboxylic acid ester with the $H_2O_2$ source. Moreover, the ratio of active compound to diluent in these solid mixtures is not economically efficient.

SUMMARY OF THE INVENTION

The object of the invention is to provide aqueous solutions of aromatic percarboxylic acids which do not have the disadvantages mentioned above and which have, in particular, an excellent long-term stability.

This object is achieved with an aqueous solution comprising an aromatic percarboxylic acid, a stabilizer for the aromatic percarboxylic acid and water, in which the stabilizer comprises:

an aromatic carboxylic acid corresponding and in an amount at least about equal in parts by weight to the aromatic percarboxylic acid; and
(i) an aqueous solution of perglutaric acid stabilized with hydrogen peroxide; and/or
(ii) a 10% to 60% aqueous solution of hydrogen peroxide.

DETAILED DESCRIPTION OF THE INVENTION INCLUDING THE PREFERRED EMBODIMENTS

It has been found, surprisingly, that the aqueous aromatic percarboxylic acid solutions of the invention as defined hereinabove are clear disinfectants of low odor, based on active oxygen compounds, having high biocidal activity and a broad spectrum of action. They are bactericidal, fungicidal, sporicidal, virus-inactivating and tuberculosis-active and can exist in an acid medium and even in a neutral medium. They can be prepared economically, do not present any safety problems, are biodegradable because their degradation products consist only of oxygen, water and organic acids, and do not cause pollution of the environment or of effluents.

The surprisingly good stabilization of the aromatic percarboxylic acids in aqueous solution is effected firstly as a result of the presence of at least approximately equal parts of the corresponding aromatic carboxylic acid and secondly as a result of the presence of a 10% to 60% strength solution of $H_2O_2$ or an aqueous solution of perglutaric acid stabilized with an excess of $H_2O_2$.

Aqueous solutions of perglutaric acid containing an excess of $H_2O_2$ and, if appropriate, also a stabilizer known for $H_2O_2$ which can be employed in the invention are described in U.S. Pat. No. 4,129,517 which is incorporated herein by reference. They contain, as a rule, 1 to 60% by weight of perglutaric acid, 1 to 50% by weight of $H_2O_2$, 0 to 50% by weight of glutaric acid, 0.01 to 2% by weight of a stabilizer such as urea or 2,3-pyridinedicarboxylic acid and/or 2,6-pyridinedicarboxylic acid and the remainder to 100% water.

Such aqueous stabilized solutions of perglutaric acid are in themselves good disinfectants, but when employed as stabilizers for the aromatic percarboxylic acids, do not produce a significant improvement in biocidal activity or an appreciably broadened spectrum of action, particularly against yeasts and fungi, and hence do not produce a synergistic increase in action.

It is particularly advantageous to employ an aqueous solution of an aromatic percarboxylic acid which has been prepared by adding an excess of 10% to 60% strength $H_2O_2$ solution to the anhydride of the aromatic carboxylic acid, a clear solution containing the aromatic percarboxylic acid and the corresponding aromatic carboxylic acid in approximately equal proportions being obtained after allowing the mixture to stand for up to 4 hours. The reaction takes place in accordance with the following equation, in which R is an aromatic radical:

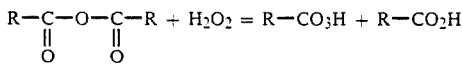

It is also possible to use, instead of the carboxylic anhydride, the corresponding aromatic peroxide

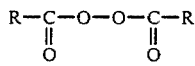

wherein R is an aromatic radical, from which an aromatic percarboxylic acid is formed with $H_2O_2$ and an aromatic carboxylic acid is formed with $H_2O$.

If the stabilization of the aromatic percarboxylic acid is to be effected not only by means of the corresponding aromatic carboxylic acid and $H_2O_2$, but also by means of the solution of perglutaric acid, not only the aromatic carboxylic acid anhydride but also glutaric anhydride are employed in the above described reaction.

It is possible, of course, to add other aromatic carboxylic acids in the preparation of the aromatic percarboxylic acid via the aromatic carboxylic anhydride, but the increase in action caused by perglutaric acid is considerably greater, from which it is assumed that the perglutaric acid solution has a solubilizing action on aromatic carboxylic anhydrides which results in the surprising increased solubility of benzoic anhydride or the reaction product of the latter with $H_2O_2$.

It is also possible, in accordance with the invention, to add further organic or inorganic acids.

Thus it is possible to add aromatic carboxylic acids in addition to carboxylic acids of the type corresponding to the aromatic percarboxylic acid. These acids also act as a stabilizer.

It is also possible to increase the stability under cold conditions or to achieve a reduction in the crystallization temperature of the formulations by adding aliphatic carboxylic acids thereto. The stability under cold conditions is improved by adding small amounts of acetic acid and/or peracetic acid or propionic acid and/or perpropionic acid. Furthermore, by adding such short-chain aliphatic acids or peracids their odor is reduced, which can be explained on the basis that more volatile compounds of the following formula:

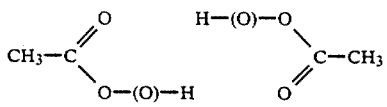

are replaced by less volatile compounds of the following formula:

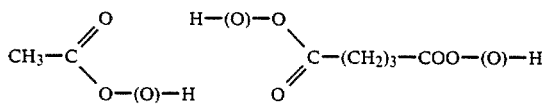

As aromatic percarboxylic acids or aromatic carboxylic anhydrides, from which the aromatic percarboxylic acids and aromatic carboxylic acids are formed by reaction with $H_2O_2$, there can be employed benzoic anhydride, which is preferred, as well as substituted benzoic anhydrides such as 4-methyl-,4-tert-butyl, 4-methoxy-, 3-chloro-, 2-methyl-, 3-methyl-, 4-cyano-, 4-nitro-, 4-fluro-, 2,4-dichloro-, 4-phenyl-, 4-methoxycarbonyl-, and 4-trifluoromethyl-benzoic anhydride, each of which yields the corresponding benzoic acid and perbenzoic acid. It is also possible to employ the following anhydrides: phthalic anhydride, which forms monoperphthalic acid and phthalic acid, 2-naphthoic anhydride, which forms 2-pernaphthoic acid and 2-naphthoic acid, 2-furancarboxylic anhydride, which forms 2-furanperoxycarboxylic acid and 2-furancarboxylic acid, and also o-sulfobenzoic cyclo-anhydride, which forms 2-sulfoperbenzoic acid and 2-sulfobenzoic acid.

It is also possible to employ mixed aromatic carboxylic anhydrides, which afford the following reaction products:

| | | |
|---|---|---|
| 2-Carboxy-benzoic anhydride | benzoic acid + phthalic acid | perbenzoic acid + monoperphthalic acid |
| 4-Sulfo-benzoic anhydride | benzoic acid + 4-sulfo-benzoic acid | perbenzoic acid + 4-sulfo-perbenzoic acid |
| Acetic/benzoic anhydride | benzoic acid + acetic acid | perbenzoic acid + peracetic acid |
| Succinic/benzoic anhydride | benzoic acid + succinic acid | perbenzoic acid + persuccinic acid |
| Glutaric/benzoic anhydride | benzoic acid + glutaric acid | perbenzoic acid + perglutaric acid |

Benzoic anhydride or perbenzoic acid is preferred because the solutions containing active oxygen, which inherently have a corrosive action on metal, have less corrosive action because of the benzoic acid which is known as a corrosion inhibitor.

In general, inorganic or organic acids stable to oxidation and of low odor which can be added are sulfuric acid, phosphoric acid, potassium bisulfate and sulfuric acid and also succinic acid or citric acid. These acids also act as a pH regulator, a cleansing component or an electrolyte for enabling metered addition to be controlled via conductance.

The aqueous solutions of aromatic percarboxylic acids according to the invention also can contain biocidal compounds stable to oxidation, such as monoperoxysulfuric acid, potassium peroxymonosulfate, persuccinic acid, peradipic acid and permaleic acid; it is also possible to employ peracetic acid and perpropionic acid, which are preferred and are employed in a low concentration in order not to affect the odor of the agent too adversely. Such compounds can be employed in amounts up to about 5% by weight of the solution. Stabilizers used for the aromatic percarboxylic acid solutions according to the invention are 2,6-pyridinedicarboxylic acid, 2,3-pyridinedicarboxylic acid and urea and also t-butanol and t-amyl alcohol, which can also function as a solubilizer.

The solutions according to the invention can also contain surfactants, specifically nonionic surfactants, such as dodecyl, nonylphenol and coconut fatty acid polyglycol ethers, and also coconut fatty acid monoethanolamide, fluorinated alkylpolyoxyethyleneethanol and ethylene/propylene oxide block polymers, and anionic surfactants, such as sodium laurylsulfate, dodecylbenzenesulfonic acid and the sodium salt thereof, sodium alkylpolyglycol ether sulfate and ether phosphate, sodium stearate, potassium perfluorooctylcarboxylate and perfluorooctanesulfonic acid; suitable cationic surfactants are, inter alia, dimethyldidecylammonium chloride, benzyldimethyl-fatty-alkylammonium sulfate, dodecyltrimethylammonium acetate, polyhexamethylenebiguanide chloride and coconut oil propylenediamineguanidinium acetate, and suitable amphoteric surfactants are dodecyldi-(aminoethyl)-glycine and lauryl-amidopropyl-N,N-dimethylaminoacetic acid.

In addition to corrosion inhibitors, such as toluenetriazole, benzotriazole and diethylenediaminepentamethylenephosphoric acid, it is also possible to add other customary additives, such as perfumes, dyestuffs and substances for controlling the pH.

The aqueous solutions of aromatic percarboxylic acids according to the invention can be employed as acidic or neutral liquid disinfectants, for example for previously cleaned surfaces or surfaces having a low to medium loading of dirt, as well as disinfectants for the skin, the mucous membranes or the hands. These solutions can also be used for improving the microbiological quality of water, in particular for improving the quality of effluents and reducing the C.O.D. and B.O.D. values, and also as bleaching agents and oxidizing agents, for odor improvement, as agents for combating plant-pathogenic microbes and viruses, for soil sterilization, as timber preservatives and for reducing the germ content of the atmosphere, for example in air conditioning plants. They are also suitable for use as additives to cleansing and/or disinfecting agents because they increase microbicidal activity or broaden the spectrum of action. They can also be employed as oxidizing agents in the blood test reaction using, for example, guaiac resin.

The following examples are illustrative of the solution of the invention without, however, being limited thereto.

EXAMPLE 1

An aqueous solution of a stabilized aromatic percarboxylic acid was prepared by mixing 0.2 part by weight of benzoic anhydride and 0.2 part by weight of 2,6-pyridinedicarboxylic acid as a further stabilizer with 99.6 parts by weight of a 35% $H_2O_2$ solution and stirring the mixture either for 48 hours at room temperature or for 5 hours at 40° C. A clear, colorless, virtually odorless solution was obtained. This solution of aromatic percarboxylic acid, which now contained perbenzoic acid and benzoic acid, was formulated by means of suitable additives to give a disinfectant or bleaching agent or oxidizing agent.

EXAMPLE 2

10 parts by weight of glutaric anhydride and 0.5 part by weight of benzoic anhydride, together with 0.2 part by weight of 2,6-pyridinedicarboxylic acid, were made up to 100 parts by weight with 35% $H_2O_2$ solution, and the mixture was stirred for 24 hours at room temperature or for 4 hours at 40° C., whereupon a clear, colorless solution of low odor was obtained; this is used as a starting solution for disinfectants.

COMPARISON TEST 1

Three solutions containing 35% strength $H_2O_2$ were made up. The first solution (A), which is in accordance with the invention, contained benzoic anhydride in an amount of 0.5% by weight. The second solution (B) contained, for comparison, 0.5% by weight of benzoic acid. Each of solutions A and B also contained 0.2% by weight of 2,6-pyridinedicarboxylic acid as stabilizer. The third solution (C) contained 0.2% by weight of pyridine-2,6-dicarboxylic acid as stabilizer. The three solutions were filtered after being stirred at room temperature for 48 hours. The pH values of these solutions were 3.81 (for A), 3.82 (for B) and 4.00 (for C).

After storing the three solutions for 6 weeks at room temperature, the content of active oxygen of the solutions showed no significant change, but solution A, according to the invention, containing benzoic anhydride, from which perbenzoic acid and benzoic acid had been formed, exhibited a considerably better spectrum of antimicrobial action than did solution B containing only benzoic acid or solution C stabilized only with 2,6-pyridinedicarboxylic acid, as shown in the following table.

TABLE 1

Suspension test in accordance with the specifications of the DGHM (German Society for Hygiene and Microbiology) without serum loading and 6 weeks after making up the solution (killing time in minutes).

| Solution | initial concentration | Staph. aureus | PS. Aeruginosa | Prot. vulgaris | Cand. albicans | Asperg. niger |
|---|---|---|---|---|---|---|
| A | 2.00% | 5 | 5 | 5 | 5 | 15 |
|   | 1.00% | 5 | 5 | 5 | 5 | >60 |
|   | 0.50% | 15 | 30 | 5 | 30 | >60 |
| B | 2.00% | >60 | 5 | 5 | >60 | >60 |
|   | 1.00% | >60 | 5 | 15 | >60 | >60 |
|   | 0.50% | >60 | 60 | >60 | >60 | >60 |
| C | 2.00% | >60 | 5 | 30 | 60 | >60 |
|   | 1.00% | >60 | 5 | >60 | 60 | >60 |
|   | 0.50% | >60 | 60 | >60 | >60 | >60 |

COMPARISON TEST 2

In order to demonstrate the excellent stability, improved activity and greater spectrum of action of the solution according to the invention, an aqueous solution containing perbenzoic acid was first prepared by dissolving benzoic anhydride in 35% $H_2O_2$ together with glutaric anhydride. This solution was then compared with a solution of perglutaric acid obtained in accordance with U.S. Pat. No. 4,129,517 (solution D) merely by adding glutaric anhydride to 35% $H_2O_2$, and was also compared with a similar perglutaric acid solution containing in addition benzoic acid (solution E). The details of the compositions of the test solutions are as follows:

| Composition | Solution according to the invention | Solution D | Solution E |
|---|---|---|---|
| Benzoic anhydride | 0.5 | | |
| Glutaric anhydride | 10 | 10 | 10 |
| Benzoic acid | — | — | 0.5 |
| 2,6-Pyridine-dicarboxylic acid | 0.2 | 0.2 | 0.2 |
| 35% $H_2O_2$ | ad 100 | ad 100 | ad 100 |

Table II shows the results, in minutes of killing time, obtained with the above suspension tests, as specified by DGHM, without serum loading; the solutions had been stored at room temperature for 19 months.

TABLE II

| Solution employed | Initial concentration | Staph aureus | Cand. albicans |
|---|---|---|---|
| according to | 2 | 5 | 5 |

TABLE II-continued

| Solution employed | Initial concentration | Staph aureus | Cand. albicans |
|---|---|---|---|
| invention | 1 | 5 | 5 |
| | 0.5 | 5 | 5 |
| | 0.25 | 5 | 5 |
| | 0.1 | 5 | 5 |
| Solution D | 2 | 5 | 15 |
| | 1 | 5 | 30 |
| | 0.5 | 5 | >60 |
| | 0.25 | 5 | >60 |
| | 0.1 | 5 | >60 |
| Solution E | 2 | 5 | 15 |
| | 1 | 5 | 15 |
| | 0.5 | 5 | 30 |
| | 0.25 | 5 | >60 |
| | 0.1 | 5 | >60 |

The figures in Table II show clearly that very much better results are obtained in the case of Candida albicans using the solution of aromatic percarboxylic acid according to the invention.

The $H_2O_2$ content of the solution was also determined after storage for 19 months at room temperature, and it was found that the solution according to the invention had, as before, a high content of $H_2O_2$ of 26.0%, compared with a value of 23.7 and 25.5% for the solutions D and E respectively.

What is claimed is:

1. A stabilized aqueous disinfecting and bleaching solution comprising an aromatic percarboxylic acid, a stabilizer for the aromatic percarboxylic acid and water, in which the stabilizer comprises:
   an aromatic carboxylic acid corresponding to the aromatic percarboxylic acid and in an amount at least about equal in parts by weight to the aromatic percarboxylic acid; and at least one of
   (i) an aqueous solution of perglutaric acid stabilized with an excess of hydrogen peroxide; or
   (ii) a 10% to 60% aqueous solution of hydrogen peroxide.

2. The stabilized aqueous disinfecting and bleaching solution of claim 1 wherein the aromatic percarboxylic acid is selected from the group consisting of perbenzoic acid, 4-tert-butylperbenzoic acid, 4-methoxyperbenzoic acid, 2-methylperbenzoic acid, 3-methylperbenzoic acid, 4-methylperbenzoic acid, 4-cyanoperbenzoic acid, 4-nitroperbenzoic acid, 3-chloroperbenzoic acid, 2,4-dichloroperbenzoic acid, 4-fluoroperbenzoic acid, 4-phenylperbenzoic acid, 4-methoxycarbonylperbenzoic acid, 4trifluoromethylperbenzoic acid, 2-sulfoperbenzoic acid, 4-sulfoperbenzoic acid, monoperphthalic acid, 2pernaphthoic acid and 2furanperoxycarboxylic acid.

3. The stabilized aqueous disinfecting and bleaching solution of claim 1 wherein, based on the weight of the stabilized aqueous disinfecting and bleaching solution the aromatic percarboxylic acid and the corresponding aromatic carboxylic acid each is present in an amount of from about 0.001 to about 2 percent by weight and wherein the stabilizer consists essentially of the corresponding aromatic carboxylic acid and the aqueous perglutaric acid solution, the aqueous perglutaric acid being present in an amount of from about 5 to about 35 present by weight.

4. The stabilized aqueous disinfecting and bleaching solution of claim 3 wherein the aromatic percarboxylic acid is present in an amount of from about 0.05 to about 0.5 percent by weight, the corresponding aromatic carboxylic acid is present in an amount of from about 0.05 to about 1 percent by weight and the aqueous perglutaric acid solution is present in an amount of from about 10 to about 20 percent by weight.

5. The stabilized aqueous disinfecting and bleaching solution of claim 1 wherein based on the weight of the stabilized aqueous disinfecting and bleaching solution the aromatic percarboxylic acid and the corresponding aromatic carboxylic acid each is present in an amount of from about 0.001 to about 0.5 percent by weight and wherein the stabilizer consists essentially of the corresponding aromatic carboxylic acid and a 10% to 60% aqueous solution of hydrogen peroxide.

6. The stabilized aqueous disinfecting and bleaching acid solution of claim 5 wherein the aromatic percarboxylic acid is present in an amount of about 0.01 to about 0.2 percent by weight and the corresponding aromatic carboxylic acid is present in an amount of about 0.01 to about 0.5 percent by weight and wherein the concentration of the hydrogen peroxide solution is 20% to 30%.

7. The stabilized aqueous disinfecting and bleaching acid solution of claim 1 wherein the aromatic percarboxylic acid is perbenzoic acid.

* * * * *

UNITED STATES PATENT AND TRADEMARK OFFICE
CERTIFICATE OF CORRECTION

PATENT NO. : 4,917,815
DATED      : April 17, 1990
INVENTOR(S) : Wolfgang Beilfuss et al It is certified that error appears in the above-identified patent and that said Letters Patent is hereby corrected as shown below:

Col. 8, line 5, the part reading

"2pernaphthoic acid and 2furanperoxycarboxylic"

should read

--2-pernaphthoic acid and 2-furanperoxycarboxylic--

Signed and Sealed this

Second Day of July, 1991

Attest:

HARRY F. MANBECK, JR.

*Attesting Officer*　　　*Commissioner of Patents and Trademarks*